United States Patent [19]
Zare et al.

[11] Patent Number: 5,912,740
[45] Date of Patent: Jun. 15, 1999

[54] RING RESONANT CAVITIES FOR SPECTROSCOPY

[75] Inventors: Richard N. Zare, Stanford, Calif.; Juergen Martin, Jena-Wogau, Germany; Barbara A. Paldus, Stanford; Jinchun Xie, Sunnyvale, both of Calif.

[73] Assignee: The Board of Trustees of the Leland Stanford Junior University, Stanford, Calif.

[21] Appl. No.: 08/879,975

[22] Filed: Jun. 20, 1997

[51] Int. Cl.$^6$ .................................................. G01N 21/61
[52] U.S. Cl. .......................................... 356/437; 356/440
[58] Field of Search ..................................... 356/440, 432, 356/439, 437; 250/343

[56] References Cited

U.S. PATENT DOCUMENTS

| | | | |
|---|---|---|---|
| 5,173,749 | 12/1992 | Tell et al. | 356/437 |
| 5,414,508 | 5/1995 | Takahashi et al. | 356/440 |
| 5,432,610 | 7/1995 | King et al. | 356/432 |
| 5,528,040 | 6/1996 | Lehmann | 356/439 |

OTHER PUBLICATIONS

Romanini et al. "CW cavity ring–down spectroscopy" Chemical Physics Letters 264(1977) 316–322, Jan. 10, 1997.

Drever, R. et al. Laser Phase and Frequency Stabilization Using an Optical Resonator. Applied Physics B 31, 97–105. 1983.

O'Keefe, Anthony and Deacon, David. Cavity ring–down optical spectometer for absorbtion measurements using pulsed laser sources. Rev. Sci. Instrum. 59 (12), Dec. 1988.

Zalicki, Piotr and Zare, Richard. Cavity ring–down spectroscopy for quantitative absorption measurement. J. Chem. Phys. 102 (7), Feb. 15, 1995.

*Primary Examiner*—Richard A. Rosenberger
*Attorney, Agent, or Firm*—Lumen Intellectual Property Services

[57] ABSTRACT

Ring-shaped resonant cavities for spectroscopy allow a reduction in optical feedback to the light source, and provide information on the interaction of both s- and p-polarized light with samples. A laser light source is locked to a single cavity mode. An intracavity acousto-optic modulator may be used to couple light into the cavity. The cavity geometry is particularly useful for Cavity Ring-Down Spectroscopy (CRDS).

32 Claims, 3 Drawing Sheets

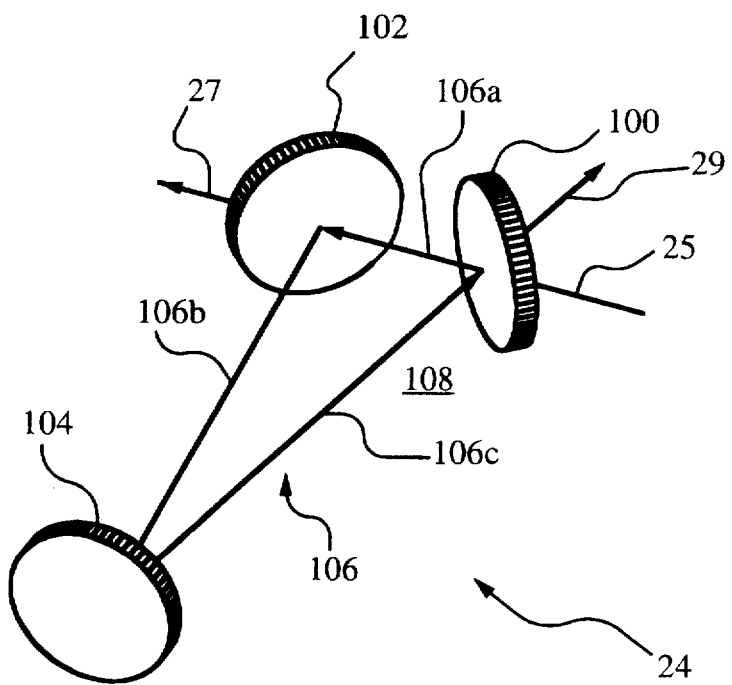
FIG. 2-A
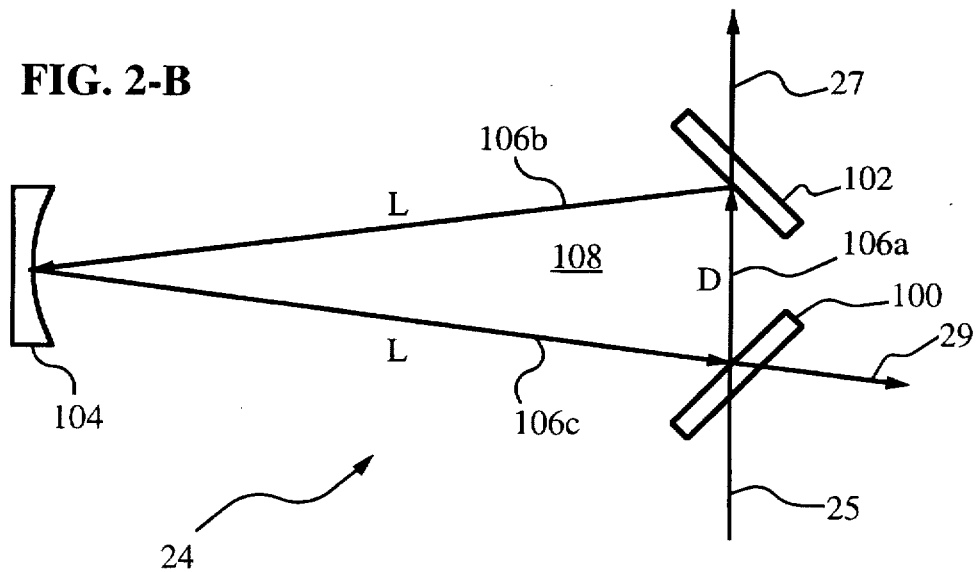
FIG. 2-B

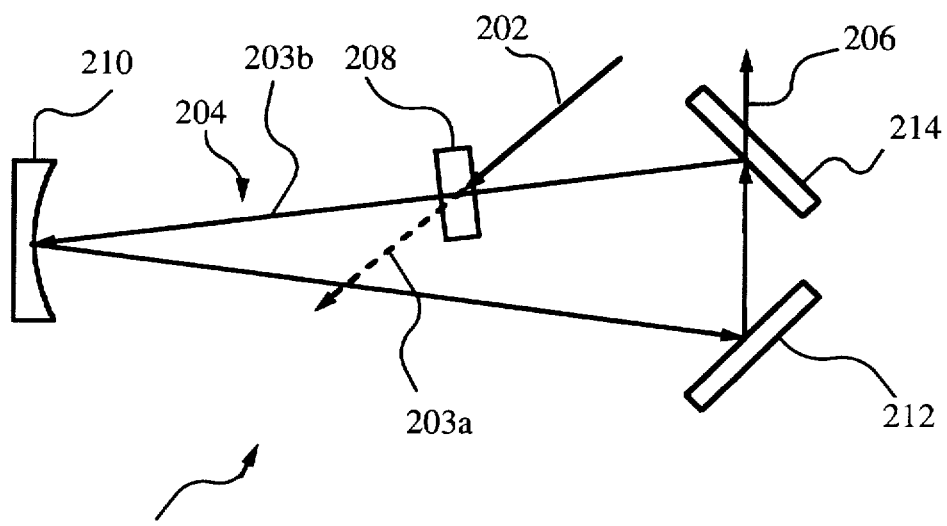
FIG. 3
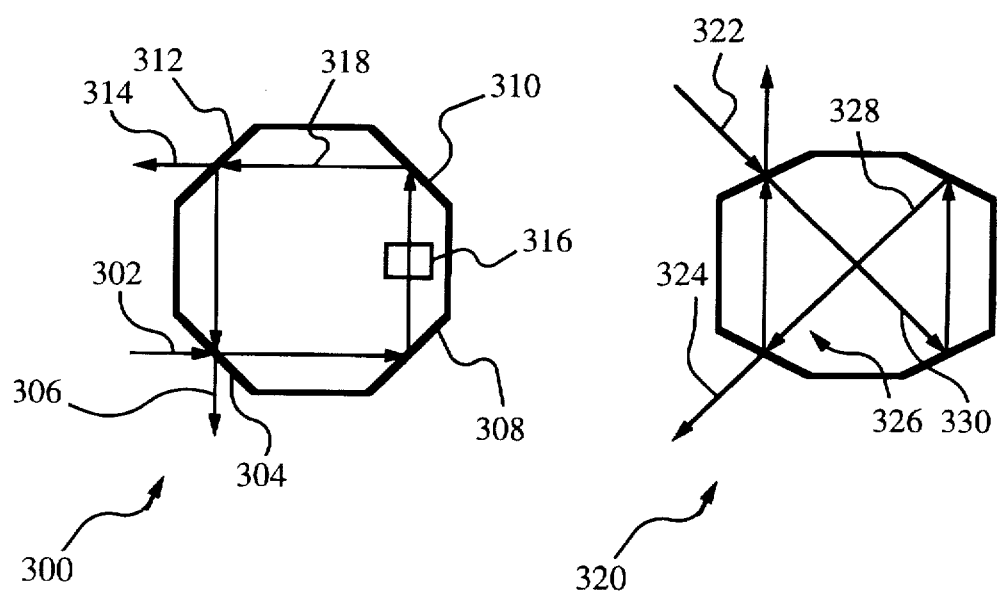
FIG. 4-A
FIG. 4-B

RING RESONANT CAVITIES FOR SPECTROSCOPY

This invention was made with U.S. Government support under grant No. DE-FG03-92ER14304, awarded by the Department of Energy. The U.S. Government has certain rights in this invention.

FIELD OF THE INVENTION

This invention relates to the field of spectroscopy, and in particular to ring configurations for laser cavities in spectroscopic applications.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light source intensity that are translated into noise in the absorption signal. For general information on traditional spectroscopy methods see for example Dereniak and Crowe, *Optical Radiation Detectors*, John Wiley & Sons, New York, 1984, and Demtroder, *Laser Spectroscopy*, Springer, Berlin, 1996.

Cavity Ring-Down Spectroscopy (CRDS), a technique first described by O'Keefe and Deacon in an article in *Rev. Sci. Instrum.* 59(12):2544–2551 (1988), allows making absorption measurements with sensitivities on the order of one part per ten million ($1:10^7$) to one part per billion ($1:10^9$) or higher. For general information on CRDS see U.S. Pat. No. 5,528,040 by Lehmann, herein incorporated by reference, as well as the articles by Romanini and Lehmann in *J. Chem. Phys.* 102(2):633–642 (1995), Meijer et al. in *Chem. Phys. Lett.* 217(1–2):112–116 (1994), Zalicki et al. in *App. Phys. Lett.* 67(1):144–146 (1995), Jongma et al. in *Rev. Sci. Instrum.* 66(4):2821–2828 (1995), and Zalicki and Zare in *J. Chem. Phys.* 102(7):2708–2717 (1995).

In a conventional CRDS system, the sample (absorbing material) is placed in a high-finesse stable optical resonator consisting of two spherical mirrors facing each other along a common optical axis. Light incident on one mirror circulates back and forth multiple times in the resonator, setting up standing waves having periodic spatial variations. Light exiting through the other mirror measures the intracavity light intensity.

The radiant energy stored in the resonator decreases in time (rings-down). For an empty cavity, the stored energy follows an exponential decay characterized by a ring-down rate that depends only on the reflectivity of the mirrors, the separation between the mirrors, and the speed light in the cavity. If a sample is placed in the resonator, the ring-down is accelerated; under suitable conditions, the intracavity energy decays almost perfectly exponentially. An absorption spectrum for the sample is obtained by plotting the reciprocal of the ring-down rate versus the wavelength of the incident light.

CRDS has been applied to numerous systems in the visible, ultraviolet, and infrared. For information on the use of CRDS for spectroscopy in the visible, see the articles by Engeln and Meijer in *Rev. Sci. Instrum.* 67(8): 2708–2713 (1996), Martin et al. in *Chem. Phys. Lett.* 258(1–2):63–70 (1996), Paul et al. in *J. Chem. Phys.* 104(8):2782–2788 (1996), Scherer et al. in *J. Chem. Phys.* 103(21):9187–9192 (1995), Scherer et al. in *J. Chem. Phys.* 102(13):5190–5199 (1995), Scherer et al. in *Chem. Phys. Lett.* 242(4–5):395–400 (1995). Heustis et al. in *Canadian J. Phys.* 72(11–12):1109–1121 (1994), and O'Keefe et al. in *Chem. Phys. Lett.* 172(3–4):214–218 (1990). Information on CRDS applications in the ultraviolet can be found in the above-referenced articles by Romanini and Lehmann, and Zalicki et al., as well as the articles by Zhu et al. in *Chem. Phys. Lett.* 257(5–6):487–491 (1996), Romanini and Lehmann in *J, Chem. Phys.* 105(1):81–88 (1996), Romanini and Lehmann in *J. Chem. Phys.* 105(1):68–80 (1996), Wahl et al. in *Diamond and Related Materials* 5(3–5):373–377 (1996), Boogaarts and Meijer in *J. Chem. Phys.* 103(13):5269–5274 (1995), Zalicki et al. in *Chem. Phys. Lett.* 234(4–6), 269–274 (1995), Jongma et al. in *J. Molecular Spectroscopy* 165(2):303–314 (1994), and Romanini and Lehmann in *J. Chem. Phys.* 99(9):6283–6301 (1993). For information on the use of CRDS for infrared spectroscopy see the above-referenced article by Martin et al., as well as the article by Scherer et al. in *Chem. Phys. Lett.* 245(2–3):273–280 (1995).

In comparison to conventional spectroscopy techniques, CRDS is advantageous because of the increased pathlength due to multiple reflections. CRDS is also advantageous because of its relative insensitivity to variations in the amplitude of light generated by the light source. In a CRDS system, fluctuations in the intensity of the light source do not typically limit sensitivity. Conventional CRDS systems are subject to optical feedback from the resonator to the light source, however. As long as the linewidth of the resonator is much narrower than the laser linewidth (as in most systems), only a small fraction of the light incident on the resonator enters the resonator; most of the light is reflected back toward the laser. Optical feedback to the laser leads to excess noise in its frequency tuning, mode oscillation stability, and power output. The excess laser noise leads in turn to unstable laser-resonator coupling, increased baseline noise, and reduced absolute sensitivity for absorption measurements.

Optical feedback from a resonant cavity to a laser is of concern for many application using linear or folded resonant cavities. For examples of non-CRDS spectroscopy systems see for example U.S. Pat. Nos. 5,173,749 and 5,432,610. A method of reducing optical feedback to the laser would find use in many non-CRDS spectroscopy applications.

OBJECTS AND ADVANTAGES OF THE INVENTION

In light of the above, it is a primary object of the present invention to provide a spectrometer comprising a ring resonant cavity. A ring cavity allows an arrangement in which light generated by a light source and incident on the cavity input is not reflected back into the light source. Consequently, relatively simple optical isolation and frequency stabilization elements may be used for the light source. The absence of feedback into the light source leads to reduced frequency fluctuations, improved light-cavity coupling, reduced baseline noise, and increased absolute sensitivity.

It is another object to provide a system comprising an intracavity input deflection means (e.g. an acousto-optic modulator) for deflecting light generated by the light source into a ring resonant cavity. The use of a deflection means for coupling light into the cavity allows coupling efficiencies (and consequently, intracavity intensities) two to three orders of magnitude higher than in systems using an input mirror for in-coupling. The higher intracavity intensity leads to improved signal to noise ratio and reduced shot noise, and allows the use of photovoltaic detectors and alternative signal processing methods.

It is another object to provide an improved cavity for cavity ring-down spectroscopy (CRDS). It is another object to provide a resonant cavity for spectroscopy, for which intracavity light consists of a traveling wave, rather than a standing wave. The use of a traveling wave allows improved uniformity in the intracavity light intensity, and consequently a reduction in inaccuracies resulting from sample burning and non-uniform sample excitation. It is yet another object to provide a spectroscopy system allowing separate analyses of sample interactions with s- and p-polarized light. Separate analyses of s- and p-polarized light are particularly useful in distinguishing between enantiomers of a species. It is still another object to provide a spectroscopy system for which s- and p-polarizations correspond to different ring-down times.

Another object is to provide for locking a laser and an external ring resonant cavity for spectroscopy, for reducing baseline noise and increasing detection sensitivity.

SUMMARY OF THE INVENTION

In the following discussion, a ring resonant cavity is understood to mean a resonant cavity comprising more than one arm, and having an output that is distinct from its input. Ring resonant cavities are distinct from linear and folded resonant cavities. Ring resonant cavities have been used previously as lasing (active) cavities.

The present invention provides an optical system comprising a light source, a ring resonant cavity in optical communication with the light source, and a detection means in optical communication with an output of the cavity. The light source generates light comprising a wavelength corresponding to an absorption region of interest of a sample. Light emitted by the light source is incident on an input of the cavity, unidirectionally follows an intracavity light path defined by the cavity, and extends from the cavity output. The intracavity light consists of a traveling wave. The sample is situated in the intracavity light path. The detection means detects the intensity of light extending from the output. The detection means is preferably capable of detecting light intensity variations in time. At any one time, the detection means selectively detects light of a given wavelength.

A wavelength tuning means varies within a range the wavelength of light sent to the detection means, for generating an absorption spectrum of the sample for the range. In a preferred embodiment, the light generated by the light source is monochromatic. The wavelength tuning means is then part of the light source, and tunes the wavelength of the light generated by the light source. Alternatively, the light generated by the light source may contain a spectrum of wavelengths (e.g. white light). The wavelength tuning means then comprises a monochromator or some other wavelength selective element for selecting only a given wavelength at a time for transmission to the detecting means.

The light source is situated such that light extending from the cavity input is not directed toward the light source. In particular, light generated by the light source is not normal to the cavity input surface, such that light reflected from the input is not directed toward the light source.

Preferably, a wavelength of light incident on the sample is in an infrared range. Infrared spectra are particularly useful for many common spectroscopy applications. The light source preferably comprises a semiconductor laser. Semiconductor lasers are advantageous because of their low cost, durability, high energy efficiency, and compatibility with optical fiber technology for remote sensing. Alternatively, the light source may comprise a pulsed dye laser or a solid state (e.g. Ti:sapphire) laser. An optical isolation means in optical communication with the laser reduces optical feedback (e.g. back-reflections) into the laser. A locking means locks the laser to a single cavity mode by stabilizing the laser and controlling the cavity shape (mirror positions). The locking means is in optical communication with the cavity, and in electrical communication with the laser and with a means for controlling the cavity shape.

A polarization control means controls the polarization of light incident on the detecting means. The polarization control means may comprise components situated anywhere from the light source to the detecting means. The polarization control means preferably controls the polarization of light incident on the cavity input. The polarization control means also contains components adapted to receive light extending from the cavity output, for controlling the polarization of light incident on the detecting means. In a preferred embodiment, the polarization control means comprises a polarization separation means in optical communication with the cavity output, for selecting light of a predetermined polarization state for transmission to the detecting means. The polarization separation means preferably sends s-polarized light to a first detector, and p-polarized light to a second detector.

The ring resonant cavity preferably comprises a moderately-reflective input mirror, a set of highly-reflective intermediate mirrors, and a moderately reflecting output mirror. The highly-reflective mirrors have substantially 100% reflectivity in the wavelength range of interest. The moderately-reflective mirrors preferably are capable of transmitting some light, and preferably have the highest non-100% reflectivity available for the wavelength range of interest. The highest-available non-100% reflectivity typically varies from 99.5% in the ultraviolet to 99.9999% in the near infrared, to 99.8% in the infrared.

The set of intermediate mirrors consists of at least one mirror. In one embodiment, the input mirror is the cavity input, while the output mirror is the cavity output. Light generated by the light source passes through the input mirror to enter the cavity, while light passing through the output mirror is incident on the detecting means. The intermediate mirrors are situated such that light passing through the input mirror is reflected sequentially by the intermediate mirrors and onto the output mirror, following the intracavity light path. Light reflected by the output mirror is incident on the input mirror, and follows the intracavity light path again. The light path preferably has a triangular shape. In one application, a reactor (e.g. an enclosure used for reactive ion etching or molecular beam epitaxy) encloses the cavity, but not the light source or the detecting means.

A data analysis means in communication with the detecting means receives a signal characterizing the intensity of light measured by the detecting means, and determines a value of a parameter of interest using the received signal. The parameter of interest is preferably a ring-down rate.

In one embodiment, an input deflection means situated in the intracavity light path deflects light generated by the light source onto the intracavity light path, such that the intracavity light follows the light path unidirectionally. The input deflection means introduces higher losses in the cavity for continuous wave light than for pulsed light, if the deflection means can be turned off faster than a pulse roundtrip time. The deflection means preferably comprises an acousto-optic modulator. The use of an intracavity deflection means allows higher intracavity intensities, and for some applications allows the use of photovoltaic detectors for detecting output light. Such detectors require relatively high light intensities for adequate operation. An intracavity modulator is also particularly useful for far-infrared applications, for which satisfactory moderately-reflecting mirrors are difficult to obtain.

DESCRIPTION OF THE FIGURES

FIG. 2-A shows a perspective view of a preferred ring resonant cavity of the present invention.

FIG. 2-B shows a top view of the cavity of FIG. 2-A.

FIG. 3 illustrates an alternative light in-coupling scheme for a cavity of the present invention.

FIG. 4-A shows a top view of an alternative cavity of the present invention.

FIG. 4-B shows a top view of another alternative cavity of the present invention.

DETAILED DESCRIPTION

Figure 1:
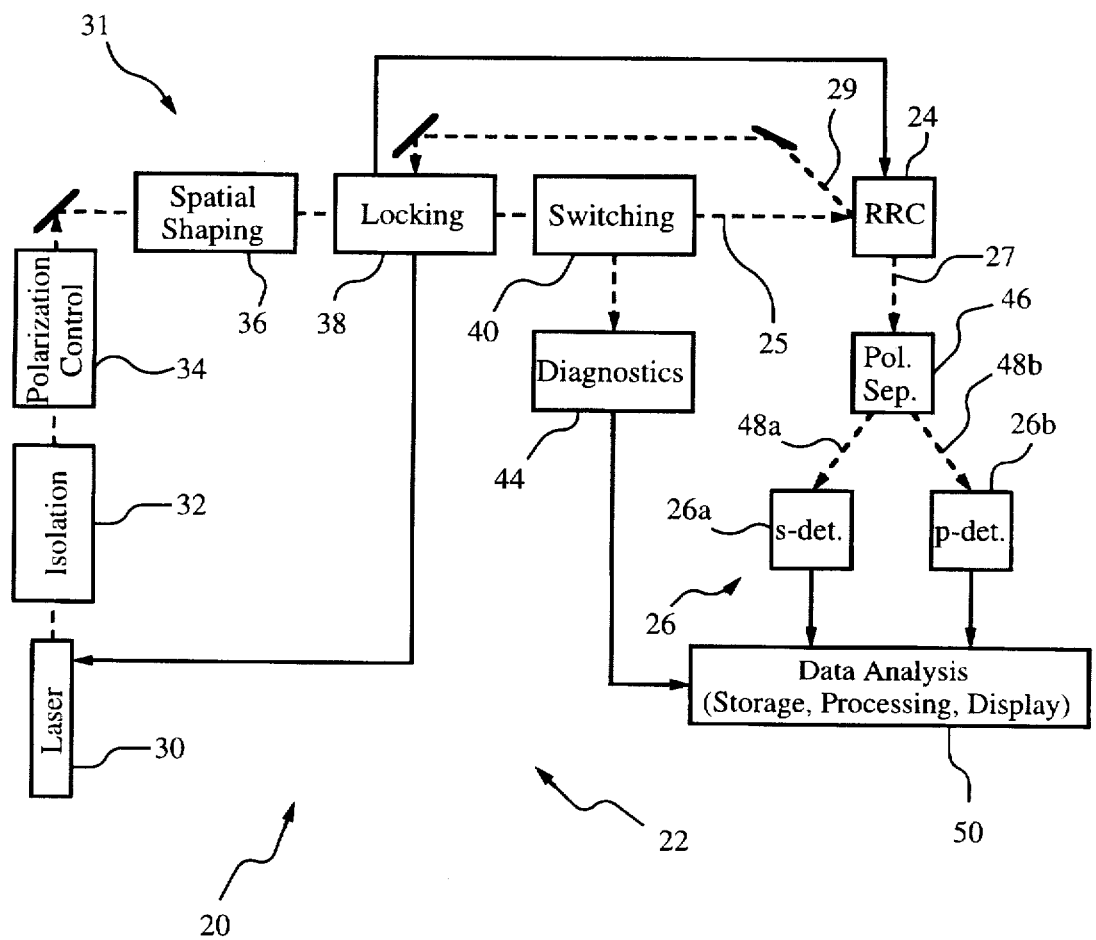
FIG. 1 is a high-level diagram of a system of the present invention.

FIG. 1 is a schematic diagram of a system 20 of the present invention. In FIG. 1, light beams are illustrated by dashed lines, while electrical connections are illustrated by solid lines. For clarity of presentation, various standard elements such as lenses and mirrors used for focusing and directing beams are not described; such elements are well known in the art.

System 20 comprises a light source 22, a mechanically-stabilized ring resonant cavity (RRC) 24 in optical communication with light source 22, and a detection means 26 in optical communication with cavity 24. Light source 22 generates an input light beam 25, which is incident on an input of cavity 24. Input beam 25 preferably consists of a continuous wave, for example a step input. Input beam 25 comprises a wavelength corresponding to an absorption region of interest of a sample. In a preferred application, input beam 25 comprises infrared light. The sample is within an intracavity light path defined by cavity 24.

Light source 22 comprises a laser 30, and a pre-cavity optical processing means 31. Laser 30 is preferably a continuous wave (c.w.) tunable infrared diode laser. Optical processing means 31 comprises components for analyzing and controlling input beam 25, including an optical isolation means 32, a polarization control means 34, a spatial shaping means 36, a locking (mode-matching) means 38, a switching means 40, and a diagnostics means 44.

Isolation means 32 reduces the optical feedback caused by back reflections into laser 30. Isolation means 32 preferably comprises a Faraday isolator. Polarization control means 34 controls the polarization of beam 25, according to the application and the information desired about the sample under analysis. Controlling polarization is well known in the art; suitable polarization control components include analyzers and compensators. Spatial shaping means 36 controls the cross-section of beam 25. In one embodiment, spatial-shaping means 36 comprises a pinhole surrounded by two lenses.

Switching means 40 preferably comprises an acousto-optic modulator for switching beam 25 on or off. Switching means 40 controls the direction (and consequently, amplitude incident on cavity 24) of beam 25, and may be used to generate pulses or continuous wave step inputs, among others. The first order beam from the acousto-optic modulator is incident on cavity 24. Diagnostic means 44 receives the zeroth order beam from the acousto-optic modulator. Diagnostic means 44 comprises multiple components optically connected in parallel to switching means 40, including a wavelength meter (alternatively, a reference cell) for calibrating the tuning of laser 30, a scanning confocal interferometer (alternatively, a photodiode connected to a spectrum analyzer) for monitoring the spectral properties of beam 25, and a CCD camera for monitoring the spatial intensity distribution of beam 25.

Locking means 38 locks light source 22 to cavity 24. In particular, locking means 38 receives an optical signal from the input of cavity 24, and sends feedback electrical signals to laser 30 for controlling the light emitted by laser 30, and to a means for controlling the resonance of cavity 24, such that the resonance of cavity 24 can follow laser drift. Locking means 38 controls laser 30 over a relatively slow time scale, and controls cavity 24 over a relatively fast time scale. The means for controlling the resonance of cavity 24 preferably comprises a piezo-electric stage for controlling the position of at least one mirror of cavity 24. Locking means 38 locks laser 30 to a predetermined transverse mode, as laser 30 is tuned. Locking means 38 helps ensure that a single mode is coupled into cavity 24. Baseline noise (or empty cavity noise) is caused primarily by excitation and beating of multiple transverse modes within cavity 24, or consecutive excitation of different transverse modes, each having different intracavity losses and consequently different ring-down constants. Excitation of multiple modes within cavity 24 would lead to decreased sensitivity in a system of the present invention.

Preferably, locking means 38 comprises a Pound-Drever stabilizer. For detailed information on Pound-Drever locking see the article by Drever et al. in *Appl. Phys.* B 31:97–105 (1983), herein incorporated by reference. A Pound-Drever stabilizer optically inserts sidebands into a laser beam by rf-modulation, and receives the laser beam reflected from the cavity. Electrical signals corresponding to the rf modulation and the reflected signal are heterodyned to generate a feedback signal which tunes the laser to a given cavity mode.

Optically connecting locking means 38 to cavity 24 is significantly simpler in a system of the present invention than in a conventional system using a linear resonant cavity. In a conventional system, the optical signal extending from the cavity input is colinear with the light beam incident on the cavity input; as a result, optical components such as half-wave plates, analyzers, and beam-splitters must be used to selectively couple the signal extending from the cavity input into the locking means.

Input beam 25 is not normal to the input of cavity 24, such that a beam 29 extending from cavity 24 is not colinear with beam 25. Beam 29 comprises a reflected component consisting of the reflection of beam 25 from the cavity input, and a "leakage" component consisting of light exiting cavity 24 through its input. Beam 29 is optically coupled into a detector of locking means 38.

The intensity of an output beam 27 extending from an output of cavity 24 is indicative of the intensity of light within cavity 24, and thus of the interaction of the sample with intracavity light. A polarization separation means 46 is used to separate the -s and p-polarized components (beams 48a, 48b, respectively) of output beam 27. More generally, polarization separation means 46 selects light of a predetermined polarization for transmission to a detector. Suitable polarization separation means may include Brewster windows, Glan-Taylor, Glan-Thomson, or Wollaston prisms, or Thomson beamsplitters, among others. A detection means 26 comprises detectors 26a, 26b in optical communication with polarization separation means 46. Detectors 26a, 26b measure the intensities of beams 48a and 48b, respectively. Detectors 26a, 26b preferably include photomultiplier tubes or avalanche photodiodes, and associated electronics (e.g. amplifiers).

A data analysis means 50 is in electrical communication with detection means 26, for receiving signals characterizing the interaction of the sample with intracavity light. Data analysis means 50 comprises a ring-down determination means for determining ring-down rates for the sample. More generally, data analysis means 50 determines a value of a parameter of interest using the signal received from detection means 26. Suitable parameters of interest include ring-down time constants and spectral distributions of absorption properties. Preferably, data analysis means 50 comprises a photon counter or integrator connected to a computer. Alternatively, data analysis means 50 may comprise electronics used for process control in a manufacturing setting. Data analysis mean s 50 is also electrically connected to diagnostics means 44, for receiving electrical signals characterizing input beam 25.

FIGS. 2-A and 2-B show perspective and top views of cavity 24, according to a preferred embodiment of the present invention. Cavity 24 comprises an input mirror 100, an output mirror 102, and an intermediate mirror 104. Cavity 24 defines a closed intracavity light path 106 comprising three arms 106a–c. A gas sample 108 is situated in the light path defined by cavity 24, and preferably fills cavity 24. Input mirror 100 and output mirror 102 are flat mirrors optimized to be highly-reflective for s-polarized light and moderately-reflective for p-polarized light at 45° incidence. Input mirror 100 and output mirror 102 are oriented at 90° relative to one another, and are situated a distance D apart. Intermediate mirror 104 is a highly-reflective spherical mirror of radius R, situated a distance L from each of mirrors 100, 102. It is preferred that L>>D, such that light incident on mirror 104 is substantially normal to mirror 104. A piezoelectric stage controlled by locking means 38 varies the relative position of mirror 104, for fast-time-scale locking of cavity 24 and laser 30.

The lengths L and D are preferably chosen relative to the radius R such that cavity 24 satisfies the stability criterion $$0 \leq g^2 \leq 1, \quad [1a]$$

with $$g = 1 - \frac{L + D/2}{R}. \quad [1b]$$

As is apparent to the skilled artisan, equations [1a] and [1b] are similar in form to the stability criterion for a linear Fabry-Perot resonator.

More generally, the geometry of a ring-resonant cavity of the present invention is chosen such that the cavity is a stable resonator. To evaluate whether an arbitrarily-shaped cavity is a stable resonator for some mode, one can resort to a generally known paraxially theory mathematically expressed in terms of ray matrices with complex-number entries (ABCD matrices). The transformation of an incident gaussian light beam by an optical element is described by an ABCD matrix; a sequence of optical elements (excluding hard-edge stops or apertures) is described by the corresponding product of ABCD matrices, which is in turn a complex ABCD matrix.

Consider a resonator exhibiting no transversely-varying gains or losses, as is typically the case for a ring resonator uniformly filled with a gas sample. The ABCD matrix entries for such a resonator are real numbers, and the total ABCD matrix can be easily calculated. The real half-trace value m of the total cavity matrix is $$m = tr\begin{pmatrix} A & B \\ C & D \end{pmatrix} = \frac{A + D}{2}. \quad [2]$$

If $|m|<1$, the resonator has at least one confined and stable gaussian mode solution. The resonator is geometrically and perturbation-stable for that mode: the mode does not geometrically diverge over a roundtrip, and an intracavity wave initially close to the stable mode will not increase its deviation from the mode over a roundtrip. For information on resonator stability considerations see chapters 19 and 21 of Siegmann, *Lasers*, University Science Books, Mill Valley, 1986.

As the skilled artisan will appreciate, as long as intracavity diffraction losses are small (as is the case if the beam size is much smaller than the sizes of intracavity optical elements), a stable, real-coefficient resonator will support higher-order Hermite-gaussian modes. Such higher-order modes damp out with a time constant determined by diffraction losses. If the higher-order mode losses are small enough, the time constant for the higher-order modes can be on the order of the ring-down constant for the mode of interest (typically, the most stable mode). It is thus desirable that locking means 38 ensure that higher-order Hermite-gaussian modes are not excited within cavity 24.

System 20 is particularly susceptible to changes in the shape of cavity 24 due to mechanical vibrations and/or temperature variations. Such changes in shape may cause drift in the mode frequencies of cavity 24. In particular, exciting a single transverse mode within cavity 24 requires that cavity 24 be sufficiently mechanically rigid. Preferably, the thermal expansion and stress tensor coefficients of cavity 24 are optimized so as to minimize cavity deformations (due to stretching, bowing, bending, etc.) and mechanical resonances. Therefore, it is preferred that the optical elements of cavity 24 are monolithically integrated. All mirrors are rigidly attached to a common thermally stabilized block of material, preferably made of a low-thermal-expansion glass such as mica ceramic. The piezoelectric stage controlling the position of mirror 104 is stably mounted on the block. The stability achieved through the monolithic linking of the mirrors, and the fast-time scale locking achieved using the piezoelectric stage ensure that the only drifts in the cavity mode frequencies are relatively slow (several hundred nm over hours). Such slow drifts are compensated for with the locking electronics connected to laser 30.

Cavity 24 is a passive cavity, i.e. is not a laser cavity with gain. In a passive cavity, the direction of the intracavity traveling wave need not be reinforced using intracavity variable loss media. Were the sample to be an active sample (e.g. having a non-linear loss or gain), spontaneous emission would be excited in all directions; generating an intracavity traveling wave would then require the use of "optical diodes," for providing high optical losses in one direction but not the other.

Light beam 25 enters cavity 24 through input mirror 100 and generates an intracavity traveling wave along light path 106. The finesse of cavity 24 is high enough that the intracavity traveling wave propagates around cavity 24 multiple times. The ring-down time constant characterizing the decay of the traveling wave in a ring cavity can be determined by applying conventional CRDS theory to the ring geometry. For a linear resonator, the ring-down time constant is given by the ratio of round trip time to total round trip losses. Analogously, the ring-down constant for a ring resonant cavity is equal to the ratio of round trip time to total round trip losses.

Consider a prior art linear resonant cavity of length L, mirror reflectivities R, sample absorption coefficient α, and sample pathlength $l_s$=L. The round-trip path length of the linear cavity is $2l_s$, while the optical loss for a round trip is $2((1-R)+\alpha l_s)$ The ring-down constant for a linear cavity is $$\tau_L = \frac{t_r}{2((1-R)+\alpha l_s)} = \frac{2L}{c} \frac{1}{2((1-R)+\alpha L)} = \frac{L}{c} \frac{1}{1-R+\alpha L} \quad [3]$$

where $t_r$ is the round trip time 2L/c.

For a ring resonant cavity formed by a triangle of arm lengths $L_1$, $L_2$, $L_3$ and mirror reflectivities R, the ring-down time constant $\tau_R$ is given by $$\tau_R = \frac{t_r}{3((1-R)+\alpha l_s)} = \frac{L_1+L_2+L_3}{c} \frac{1}{3(1-R)+\alpha(L_1+L_2+L_3)}. \quad [4]$$

With the notation $$p = \frac{L_1+L_2+L_3}{3} \quad [5]$$

eq. [4] becomes $$\tau_R = \frac{p}{c} \frac{1}{1-R+\alpha p} \quad [6]$$

which is equal to the ring-down constant for a linear resonator of length p and identical mirror reflectivities R (see eq. [3]). The additional sample pathlength of the ring cavity compensates for the additional roundtrip losses due to the increased mirror number. Note that in practice, eq. [6] needs to be modified to take into account the different reflectivities of the input and output mirrors relative to those of the intermediate mirror(s).

In general, a ring cavity configuration shaped as a N-arm polygon of arm length L will have N/2-times the losses of a linear cavity of length L, if all mirrors have identical reflectivities. The ring cavity sample length will also be N/2 times that of the linear cavity, such that the ring-down rates are identical for the ring and linear cavities.

Since longer ring-down time constants allow increased sensitivity, it is on one hand desirable that intracavity losses be minimal (see eq. [4]). On the other hand, the input and output mirrors must transmit some light, in addition to reflecting and absorbing light. Consequently, it is preferred that the intermediate mirrors in a ring cavity of the present invention are of the highest reflectivity available (typically, 100%), and that the input and output mirrors have moderate reflectivities.

Consider a wavelength range for which it is difficult to obtain mirrors that have good transmission properties. Such wavelength ranges include the mid- and far-infrared, and the ultraviolet. In such ranges, available mirrors that are not perfectly reflective have poor transmission properties and high scattering losses (T+R+S=1, where T, R, S are transmission, reflection, and scattering coeffiecients, respectively). Relative to a linear cavity, a ring-resonant cavity is particularly advantageous for applications in such wavelength ranges, where intracavity losses are dominated by losses at the input and output mirrors, and losses introduced by the intermediate mirrors are relatively insignificant. The intracavity losses of a ring cavity are then similar to those of a linear cavity having identical input and output mirrors, while the sample path length can be significantly greater, as discussed above. Consequently, a ring cavity may allow significantly longer ring-down times than a linear cavity of similar size.

The traveling nature of the intracavity light beam in a ring resonator is advantageous because of the relative uniformity of the field of traveling waves, as compared to standing waves. For a standing wave, the relatively high local variations in light intensity may lead to sample burning and artifacts due to non-uniform sample excitation.

Since light is not orthogonal to the mirrors in a ring resonant cavity, mirror reflectivities are different for s- and p-polarized light. As a result, s- and p- polarized light have different ring-down time constants in a ring resonant cavity (see Eq. [4]). Analyzing the decay of both s- and p-polarized light thus provides information that is not available in a conventional linear system. Such information may be related to the interaction of the sample with magnetic fields or mechanical stresses, or may be indicative of the molecular structure of the sample. Distinguishing between s- and p-polarized light is particularly useful for discerning enantiomers of a molecular species.

Relative to a linear cavity, a ring resonant cavity is also advantageous because of the relative ease of compensating for slight misalignments in mirror positions. In a linear cavity, a misalignment of the cavity mirrors after initial alignment requires opening the cavity to perform a new alignment. In a ring cavity, however, slight misalignments in mirror positions may be compensated for by a realignment of the input beam incidence on the cavity input. Such a realignment may not require physical access to the cavity, and can be performed by adjusting the position of an extracavity mirror.

FIG. 3 shows an alternative ring resonant cavity 200 of the present invention. Cavity 200 is particularly suited for use with a pulsed light source. An input light pulse 202 generated by a light source (not shown) is incident on cavity 200, where it generates a traveling wave propagating along an intracavity lightpath 204. Output light pulses 206 extend from cavity 200, and are incident on a detection means (not shown).

Input pulse 202 is incident on an intracavity deflection means 208. If deflection means 208 is in an off-state, pulse 202 would continue unimpeded as pulse 203a. Deflection means 208 deflects pulse 202 onto light path 204, as pulse 203b. Preferably, deflection means 208 comprises an acousto-optic modulator. Alternatively, deflection means 208 may comprise an electro-optic modulator or another device for altering the direction of input beam 202. Deflection means 208 is turned on as pulse 202 is incident on deflection means 208, but is turned off within less than a roundtrip time for lightpath 204, such that deflection means 208 does not deflect pulse 203b after one roundtrip around path 204. Pulse 203b is reflected sequentially by high-reflectivity mirrors 210, 212. Output pulses 206 exit cavity 200 through a moderate-reflectivity mirror 214. The intensity of output pulses 206 decays in time.

Input deflection means 208 may also be used to couple a continuous wave into cavity 200. Input deflection means 208 is then continuously on. In such an embodiment, deflection means 208 introduces additional losses into cavity 200, as some (but not all) intracavity light extending from mirror 214 and incident on deflection means 208 is deflected out of cavity 200.

The use of a deflection means such as an acousto-optic modulator for coupling light into cavity 200 allows relatively high in-coupling efficiencies, and correspondingly high intracavity light intensities. The use of an acousto-optic modulator allows in-coupling efficiencies of about 40%, which is two to three orders of magnitude higher than the 0.001–0.1% efficiencies achieved with typical input mirrors.

An in-coupling scheme using a deflection means is particularly useful for far-infrared spectroscopy applications, for which it is particularly difficult to manufacture mirrors that have high-reflectivity but are not perfectly reflective. For a far-infrared application, mirrors 210 and 212 are perfectly reflective, while mirror 214 has a small aperture for allowing some light to exit cavity 200. A mirror similar to mirror 214 would be difficult to use for coupling light into cavity 200.

FIG. 4-A is a top view of an alternative ring resonant cavity 300 of the present invention. An input beam 302 generated by a light source (not shown) is incident on an input mirror 304. An extracavity beam 306 extending from input mirror 304 is not colinear with beam 302. Light passing through input mirror 304 is reflected sequentially by intermediate mirrors 308, 310, and is incident on an output mirror 312. A light beam 314 extending from output mirror 312 is incident on a detection means (not shown). A sample 316 is situated in an intracavity light path 318 consisting of four arms. Light passing through input mirror 304 goes around path 318 multiple times.

FIG. 4-B is a top view of another alternative ring resonant cavity 320 of the present invention. An input light beam 322 is incident on cavity 320, while an output light beam 324 extends from cavity 320. Cavity 320 defines an intracavity light path 326 having a bowtie shape and comprising intersecting arms 328, 330.

It will be clear to one skilled in the art that the above embodiments may be altered in many ways without departing from the scope of the invention. For example, a system of the present invention may be used for applications in a wide variety of wavelength ranges, including applications using synchrotron radiation. Moreover, a system of the present invention is not limited to CRDS applications. Accordingly, the scope of the invention should be determined by the following claims and their legal equivalents.

What is claimed is:

1. An optical system for performing an absorption measurement, said system comprising:
    a) a light source for generating light comprising a wavelength corresponding to an absorption region of interest of a sample;
    b) a ring resonant cavity in optical communication with said light source, wherein said cavity defines an intracavity light path, light emitted by said light source is incident on an input of said cavity, follows said light path, and extends from an output of said cavity, and said sample is situated in said light path; and
    c) a detection means in optical communication with said output, for detecting an intensity of light of said wavelength extending from said output;
    wherein said light emitted by said light source is not normal to said input, whereby light extending from said input is directed away from said light source.

2. The system of claim 1 wherein said light source comprises a laser.

3. The system of claim 2 wherein said laser is a semiconductor laser.

4. The system of claim 3 wherein said light source further comprises a locking means in optical communication with said cavity and in electrical communication with said semiconductor laser, for locking said semiconductor laser to said cavity, thereby stabilizing said semiconductor laser.

5. The system of claim 4 wherein said locking means is in optical communication with said light extending from said input.

6. The system of claim 5 further comprising a data analysis means in electrical communication with said detection means, for receiving a signal characterizing said intensity and determining a ring-down rate using said signal.

7. The system of claim 2 wherein said light source further comprises an optical isolation means in optical communication with an output of said laser, for reducing an optical feedback to said laser.

8. The system of claim 1 further comprising a wavelength tuning means for varying said wavelength within a range, for generating an absorption spectrum of said sample for said range.

9. The system of claim 2 wherein said light source is monochromatic.

10. The system of claim 9 wherein said light source is tunable.

11. The system of claim 1 wherein said wavelength is in an infrared range.

12. The system of claim 1 wherein said cavity comprises:
    a) a moderately-reflective input mirror, wherein light generated by said light source is incident on said input mirror;
    b) a plurality of highly-reflective intermediate mirrors situated such that light passing through said input mirror is reflected sequentially by said set of intermediate mirrors, following said light path; and
    c) a moderately-reflective output mirror situated such that light extending from an intermediate mirror is incident on said output mirror, light reflected by said output mirror is incident on said input mirror, and light passing through said output mirror is incident on said detection means.

13. The system of claim 1 wherein said light path has a substantially triangular shape.

14. The system of claim 1 wherein said light path has a bowtie shape.

15. The system of claim 1 further comprising a data analysis means in electrical communication with said detection means, for receiving a signal from said detection means characterizing said intensity, and determining a value of a parameter of interest using said signal.

16. The system of claim 15 wherein said parameter of interest is a ring-down rate.

17. The system of claim 1 further comprising a reactor enclosing said cavity, wherein said light source and said detection means are situated outside said reactor.

18. The system of claim 1 wherein said light along said light path consists of a traveling wave.

19. A system for determining an optical property of a sample, said system comprising:
    a) a light source for generating light comprising a wavelength corresponding to an absorption region of interest of the sample;
    b) a ring resonant cavity in optical communication with said light source, wherein said cavity defines an intracavity light path, light emitted by said light source is incident on an input of said cavity, follows said light path, and extends from an output of said cavity, and said sample is situated in said light path;
    c) a detection means in optical communication with said output, for detecting an intensity of light of said wavelength extending from said output; and d) a polarization control means for controlling a polarization of light incident on said detection means.

20. The system of claim 19 wherein said polarization control means is adapted to control a polarization of light incident on said input.

21. The system of claim 19 wherein said polarization control means is adapted to receive light extending from said output.

22. The system of claim 21 wherein said polarization control means comprises a polarization separation means in optical communication with said output, for selecting light of a predetermined polarization state for transmission to said detection means.

23. The system of claim 19 wherein said detection means comprises:

a) a first detector in optical communication with said output, for detecting s-polarized light extending from said output; and b) a second detector in optical communication with said output, for detecting p-polarized light extending from said output.

24. An optical system for performing an absorption measurement, said system comprising:

a) a light source;

b) a ring resonant cavity defining an intracavity light path;

c) an input deflection means having an on state and an off state, wherein said input deflection means is situated within said intracavity light path such that:

(i) light generated by said light source is deflected onto said intracavity light path when said input deflection means is in said on state, such that intracavity light follows said intracavity light path unidirectionally, and (ii) said light generated by said light source is not deflected onto said intracavity light path when said input deflection means is in said off state; and d) a detection means for detecting light of a given wavelength extending from said cavity.

25. The system of claim 24 wherein said light source is adapted to generate a light pulse incident on said input.

26. The system of claim 24 wherein said input deflection means comprises an acousto-optic modulator.

27. The system of claim 24 wherein said detection means comprises a photovoltaic detector.

28. The system of claim 24 wherein said wavelength is in an infrared range.

29. The system of claim 24 wherein said light source comprises a laser.

30. An optical system for performing an absorption measurement, said system comprising:

a) a ring-down resonant cavity defining a non-linear unidirectional light path;

b) a tunable light source in optical communication with an input of said cavity such that light extending from said input is not incident on said light source, for generating light comprising a wavelength corresponding to an absorption region of interest of said sample, wherein said light of said wavelength is incident on said cavity and rings down within said cavity according to a ring-down rate determined by an absorption of said sample at said wavelength;

c) a detection means in optical communication with said cavity, for detecting a time-dependence of an intensity of light of said wavelength within said cavity; and d) a data analysis means in electrical communication with said detection means, for determining said ring-down rate from said time-dependence.

31. The system of claim 30 wherein said tunable light source comprises a diode laser, and wherein said system further comprises:

a locking means in electrical communication with said diode laser and in optical communication with said light extending from said input, for locking said diode laser to said cavity, thereby stabilizing said diode laser.

32. A method of performing an absorption measurement, comprising the steps of:

a) generating light comprising a wavelength corresponding to an absorption region of interest of a sample;

b) using said light to illuminate said sample, wherein said sample is situated within a unidirectional intracavity light path defined by a ring resonant cavity;

c) detecting an intracavity intensity of s-polarized light of said wavelength; and d) detecting an intracavity intensity of p-polarized light of said wavelength.

* * * * *